United States Patent [19]

Bishop et al.

[11] Patent Number: 5,510,383
[45] Date of Patent: Apr. 23, 1996

[54] USE OF CLOPROSTENOL, FLUPROSTENOL AND THEIR SALTS AND ESTERS TO TREAT GLAUCOMA AND OCULAR HYPERTENSION

[75] Inventors: John E. Bishop, Arlington; Louis DeSantis, Jr., Fort Worth; Verney L. Sallee, Burleson, all of Tex.

[73] Assignee: Alcon Laboratories, Inc., Fort Worth, Tex.

[21] Appl. No.: 101,598

[22] Filed: Aug. 3, 1993

[51] Int. Cl.$^6$ .................................................. A61K 31/557
[52] U.S. Cl. ........................................... 514/530; 514/573
[58] Field of Search ..................................... 514/530, 573

[56] References Cited

U.S. PATENT DOCUMENTS

| 4,599,353 | 7/1986 | Bito | 514/530 |
| 5,288,754 | 2/1994 | Woodward et al. | 514/530 |
| 5,352,708 | 10/1994 | Woodward et al. | 514/729 |

FOREIGN PATENT DOCUMENTS

| 330511A2 | 8/1989 | European Pat. Off. . |
| 364417A1 | 4/1990 | European Pat. Off. . |
| 435682A2 | 7/1991 | European Pat. Off. . |
| 90/02553 | 3/1990 | WIPO . |

OTHER PUBLICATIONS

Coleman et al., "Prostanoids and their Receptors," *Comprehensive Medicinal Chemistry*, vol. 3 (1990), 12.1:643–714.
Narumiya et al., "Structure and function of prostanoid receptors," *J. of Lipid Mediators*, 6:155–161 (1993).
Woodward et al., "Intraocular pressure effects of selective prostanoid receptor agonists involve different receptor subtypes according to radioligand binding studies," *J. of Lipid Mediators*, 6:545–553 (1993).
Bito et al., "The ocular effects of prostaglandins and the therapeutic potential of a new PGF$_{2\alpha}$ analog, PhXA41 (latanoprost), for glaucoma management," *J. of Lipid Mediators*, 6:535–543 (1993).
Resul et al., "Phenyl–Substituted Prostaglandins: Potent and Selective Antiglaucoma Agents," *J. Med. Chem.*, 36:243–248 (1993).
Stjernschantz et al., "Phenyl substituted prostaglandin analogs for glaucoma treatment," *Drugs of the Future*, 17(8):691–704 (1992).
*The Merck Index*, 11th Ed., p. 375 (1989).
Zajaez et al., "Effect on Human Eye of Prostaglandin and a Prostaglandin Analogue Used to Induce Abortion," *IRCS Medical Science: Clinical Medicine: Clinical Pharmacology & Therapeutics: Drug Metabolism & Toxicology: The Eye: Reproduction, Obstetrics & Gynecology*, 4:316 (1976).
*The Merck Index*, 11th Ed., pp. 656–657 (1989).

Primary Examiner—Richard L. Raymond
Attorney, Agent, or Firm—James A. Arno; Barry L. Copeland; Julie J. L. Cheng

[57] ABSTRACT

Disclosed is the use of cloprostenol, fluprostenol, and their pharmaceutically acceptable salts and esters for the treatment of glaucoma and ocular hypertension. Also disclosed are ophthalmic compositions comprising said compounds.

20 Claims, 3 Drawing Sheets

USE OF CLOPROSTENOL, FLUPROSTENOL AND THEIR SALTS AND ESTERS TO TREAT GLAUCOMA AND OCULAR HYPERTENSION

BACKGROUND OF THE INVENTION

The present invention relates to the treatment of glaucoma and ocular hypertension. In particular, the present invention relates to the use of cloprostenol, fluprostenol, and their pharmaceutically acceptable salts and esters to treat glaucoma and ocular hypertension.

Cloprostenol and fluprostenol, both known compounds, are synthetic analogues of $PGF_{2\alpha}$, a naturally-occurring F-series prostaglandin (PG). Structures for $PGF_{2\alpha}$, cloprostenol, and fluprostenol, are shown below:

$PGF_{2\alpha}$:

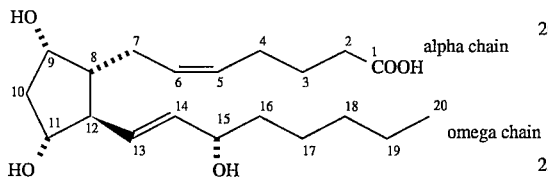

Cloprostenol:

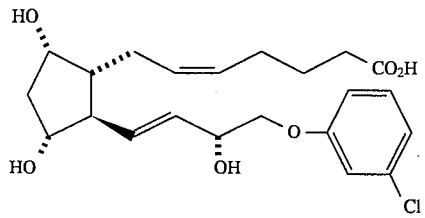

Fluprostenol:

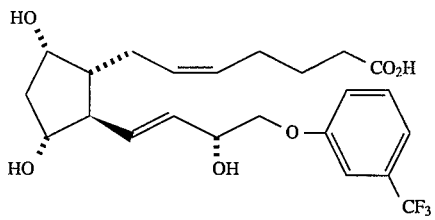

The chemical name for cloprostenol is 16-(3-chlorophenoxy)-17, 18, 19, 20-tetranor $PGF_{2\alpha}$. Monograph No. 2397 (page 375) of *The Merck Index,* 11th Edition (1989) is incorporated herein by reference to the extent that it describes the preparation and known pharmacological profiles of cloprostenol. Fluprostenol has the chemical name 16-(3-trifluoromethylphenoxy)-17, 18, 19,20-tetranor $PGF_{2\alpha}$. Monograph No. 4121 (pages 656–657) of *The Merck Index,* 1 lth Edition (1989) is incorporated herein by reference to the extent that it describes the preparation and known pharmacological profiles of fluprostenol. Cloprostenol and fluprostenol are 16-aryloxy PGs and, in addition to the substituted aromatic ring, differ from the natural product, $PGF_{2\alpha}$ in that an oxygen atom is embedded within the lower (omega) chain. This oxygen interruption forms an ether functionality.

Naturally-occurring prostaglandins are known to lower intraocular pressure (IOP) after topical ocular instillation, but generally cause inflammation, as well as surface irritation characterized by conjunctival hyperemia and edema.

Many synthetic prostaglandins have been observed to lower intraocular pressure, but such compounds also produce the aforementioned side effects. Various methods have been used in attempting to overcome the ocular side effects associated with prostaglandins. Stjernschantz et al. (EP 364 417 A1 ) have synthesized derivatives or analogues of naturally-occurring prostaglandins in order to design out selectively the undesired side effects while maintaining the IOP-lowering effect. Others, including Ueno et al. (EP 330 511 A2) and Wheeler (EP 435 682 A2) have tried complexing prostaglandins with various cyclodextrins.

The Stjernschantz et al. publication is of particular interest, as it demonstrates that certain synthetically-modified $PGF_{2\alpha}$ analogues retain the potent IOP-lowering effect of the parent ($PGF_{2\alpha}$ isopropyl ester) while decreasing the degree of conjunctival hyperemia. In this publication, the only modification to the PG structure is to the omega chain: the chain length is 4–13 carbon atoms ."optionally interrupted by preferably not more than two heteroatoms (O, S, or N)" and includes a phenyl ring (substituted or unsubstituted) on the terminus (see page 3, line 44 to page 4, line 7). Stjernschantz et al. exemplify two subclasses within this definition:

(1) carbon-only omega chains, i.e.,

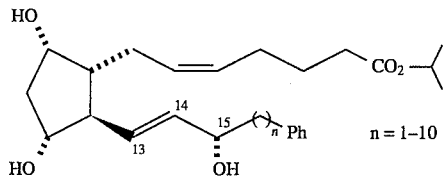

and (2) heteroatom-interrupted omega chains, i.e.,

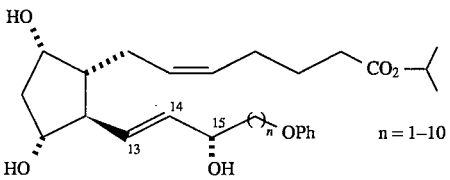

In particular, the 17-phenyl-18, 19,20-trinor analogue of $PGF_{2\alpha}$ isopropyl ester (formula 1, n=2) displayed a superior separation of toward and untoward activities. Furthermore, the 13, 14-dihydro analogue of 17-phenyl-18, 19,20-trinor $PGF_{2\alpha}$ isopropyl ester displayed an even more favorable separation of activities. Both 17-phenyl $PGF_{2\alpha}$ and its 13, 14-dihydro congener fall into the former (formula 1, carbon-only omega chain) subclass. Additional synthetic analogues employing the phenyl substituent on the end of the omega chain explored the effects of chain elongation, chain contraction, and substitution on the phenyl ring. However, such analogues showed no apparent therapeutic improvement over the preferred formulation, 13, 14-dihydro-17-phenyl-18, 19,20-trinor $PGF_{2\alpha}$ isopropyl ester.

Because they contain heteroatom (O) interruption of the omega chain, both cloprostenol and fluprostenol are generically included in the subclass defined in formula 2 by Stjernschantz et al. However, neither compound is specifically mentioned by Stjernschantz et al. and the disclosure is primarily related to carbon-only omega chains. The only example of a heteroatom-interrupted omega chain disclosed by Stjernschantz et al. is 16-phenoxy-17,18,19,20 tetranor $PGF_{2\alpha}$ isopropyl ester (see formula 2, n=1). The IOP data revealed by Stjernschantz et al. for 16-phenoxy-17, 18, 19,20-tetranor $PGF_{2\alpha}$ isopropyl ester (see Stjernschantz et al, page 17, Table V) indicate an initial increase in IOP (1–2 hours after administration) followed by a decrease. Moreover, this compound displays unacceptable hyperemia (see Stjernschantz et al., Table IV, line 40). In short, data from Stjernschantz et al. demonstrate that the oxygen-interrupted omega chain subgeneric class of compounds (see formula 2) displays an unacceptable therapeutic profile.

SUMMARY OF THE INVENTION

It has now been unexpectedly found that cloprostenol, fluprostenol, and their pharmaceutically acceptable salts and esters show significantly greater IOP reduction than the compounds of Stjernschantz et al., while having a similar or lower side effect profile. In particular, it appears that the addition of a chlorine atom or a trifluoromethyl group to the meta position on the phenoxy ring at the end of the omega chain provides a compound having excellent IOP reduction without the significant side effects found with other, closely related compounds.

DETAILED DESCRIPTION OF THE INVENTION

Figure 1:
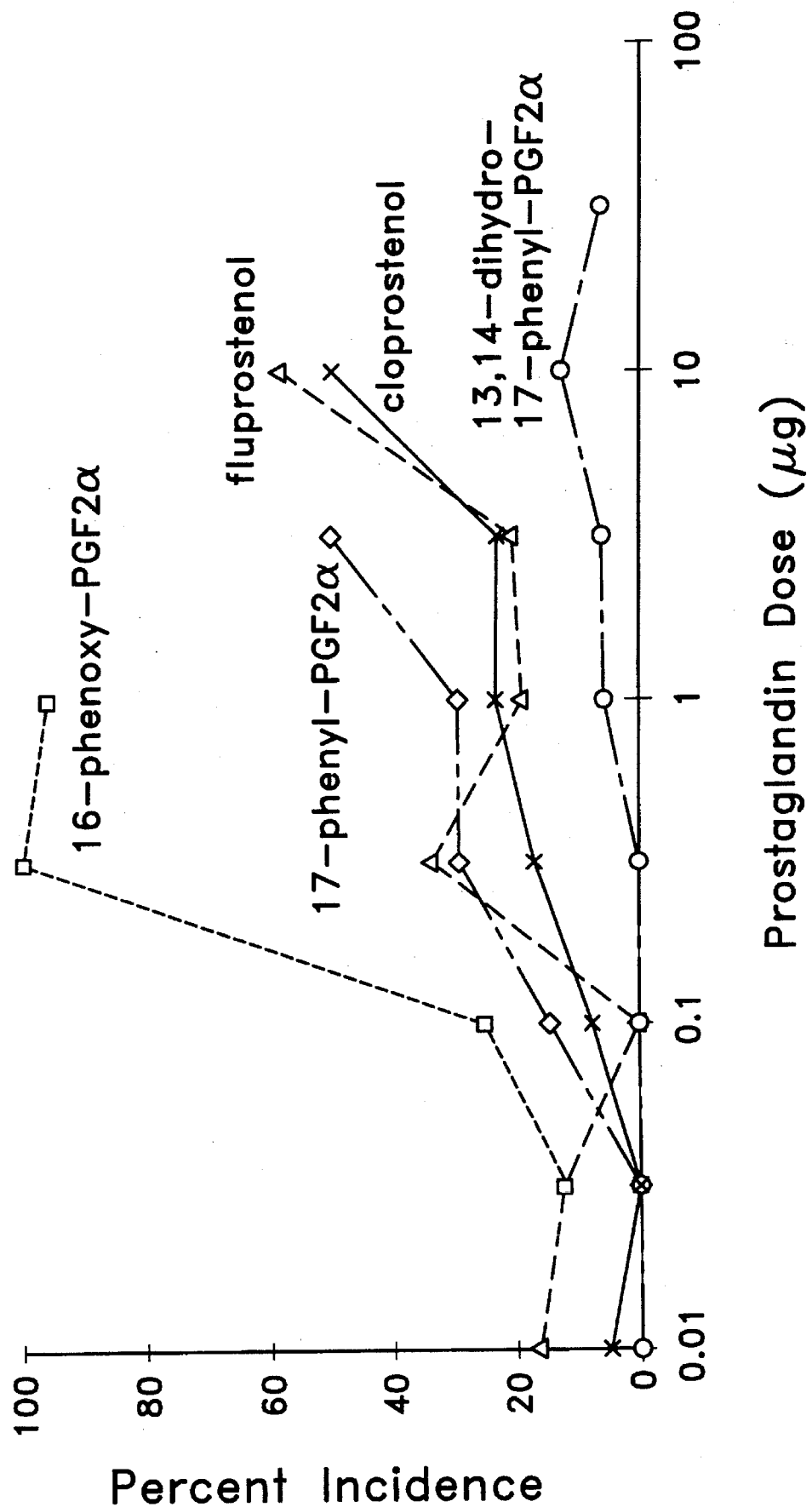
FIG. 1 is a graph showing the relative hyperemia scores (cumulative) of five tested compounds (see Table 1, below), two of which are compounds of the present invention.

The compounds useful in the present invention have the following general formula:

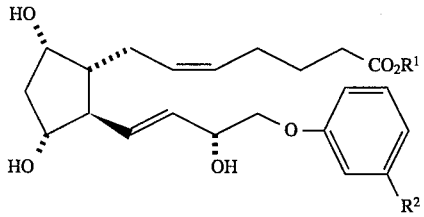

wherein: $R^1$=hydrogen, a cationic salt moiety, a pharmaceutically acceptable amine moiety or $C_1$–$C_{12}$ alkyl, cycloalkyl or aryl; and $R^2$=Cl or $CF_3$.

The compounds of the present invention include the free acid, alkali and alkaline earth metal salts, ammonium and amine salts, and esters. Preferred salts are those involving alkali and alkaline earth metal cations, particularly sodium and potassium, and amine salts, especially the tris(hydroxymethyl)aminomethane ("tromethamine") salts. Preferred esters are $C_1$–$C_{12}$ alkyl esters, particularly straight or branched $C_1$–$C_6$ alkyl esters, especially methyl, ethyl, isopropyl, cyclopropyl, cyclopropyl methyl, butyl, cyclobutyl, isobutyl, t-butyl or pentyl. Particularly preferred compounds of formula (I) are the sodium and tromethamine salts (R=$Na^+$, $CH_3N^+(CH_2OH)_3$) and the methyl, isopropyl, and t-butyl esters (R=$CH_3$, $CH(CH_3)_2$, $C(CH_3)_3$).

Alkali metal salts and alkaline earth metal salts may be formed conventionally from the acid form. The acid may be converted to the ester by conventional condensation with an alcohol (e.g., $C_1$–$C_3$ alkyl alcohol) or by reaction with an alkyl electrophile (e.g., $C_1$–$C_3$ alkyl iodide) in the presence of base, according to known procedures. In a similar manner, other esterifications may be effected as is known in the art employing other low alkyl, cycloalkyl, cycloalkyalkyl, aryl, or arylalkyl alcohols and/or halides such as isopropanol, cyclopropanol, cyclopropylmethanol, or phenyl or benzyl alcohol or iodide. Since such esterification reactions are well known, they are not further described here.

The compounds of formula (I) are useful in lowering intraocular pressure and thus are useful in the treatment of glaucoma. The preferred route of administration is topical. The dosage range for topical administration is generally between about 0.001 and about 1000 micrograms per eye (μg/eye) and is preferably between about 0.01 and about 100 μg/eye and most preferably between about 0.05 and 10 μg/eye. The compounds of the present invention can be administered as solutions, suspensions, or emulsions (dispersions) in a suitable ophthalmic vehicle.

In forming compositions for topical administration, the compounds of the present invention are generally formulated as between about 0.0002 to about 0.02 percent by weight (wt %) solutions in water at a pH between 4.5 to 8.0. The compounds are preferably formulated as between about 0.001 to about 0.01 wt % and, most preferably, between about 0.001 and about 0.005 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives:

Ophthalmic products are typically packaged in multidose form, which generally require the addition of preservatives to prevent microbial contamination during use. Suitable preservatives include: benzalkonium chloride, thimerosal, chlorobutanol, methyl paraben, propyl paraben, phenylethyl alcohol, edetate disodium, sorbic acid, ONAMER M, or other agents known to those skilled in the art. Such preservatives are typically employed at a concentration between about 0.001% and about 1.0% by weight.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; cyclodextrins; or other agents known to those skilled in the art. Such co-solvents are typically employed at a concentration between about 0.01% and about 2% by weight.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a concentration between about 0.01% and about 2% by weight.

The studies detailed in the following Examples 1–4 compared the IOP lowering activity and side effects of five compounds: A) Cloprostenol, isopropyl ester; B) Fluprostenol, isopropyl ester; C) 16-Phenoxy-17, 18, 19,20-tetranor $PGF_{2\alpha}$, isopropyl ester; D) 17-Phenyl-18, 19,20-trinor $PGF_{2\alpha}$, isopropyl ester; and E) 13,14-Dihydro-17-phenyl-18,19,20-trinor $PGF_{2\alpha}$, isopropyl ester (latanoprost). The structures of these compounds are shown in the following Table 1.

nation and scores for conjunctival hyperemia were recorded for upper bulbar conjunctiva according to the following criteria:

0=Normal appearance of vessels at timbus and on superior rectus muscle

+1=Enlargement of vessels normally visible at limbus and on superior rectus muscle +2=Branch of vessels at limbus, new vessels visible +3=New vessels visible in open bulbar conjunctival areas +4=Diffuse redness in open bulbar conjunctival areas

TABLE 1

| | COMPOUND NAME | COMPOUND STRUCTURE |
|---|---|---|
| A | Cloprostenol, isopropyl ester | 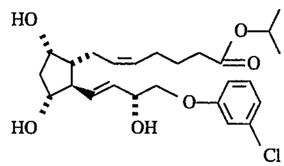 |
| B | Fluprostenol, isopropyl ester | 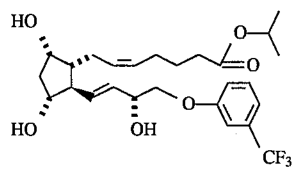 |
| C | 16-Phenoxy-17,18,19,20-tetranor $PGF_{2\alpha}$, isopropyl ester | 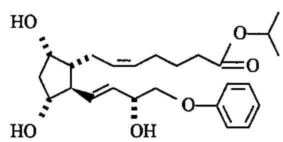 |
| D | 17-Phenoxy-18,19,20-trinor $PGF_{2\alpha}$, isopropyl ester | 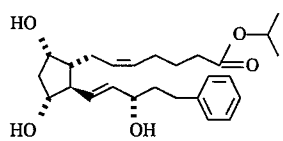 |
| E | 13,14-Dihydro-17-phenyl-18,19,20-trinor $PGF_{2\alpha}$, isopropyl ester | 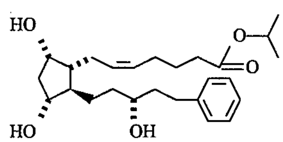 |

As is apparent in Table 1, the five compounds differ only slightly in structure; however, as Examples 1 and 2 will show, such seemingly slight structural differences produce greatly different IOP-lowering effects and levels of hyperemia.

EXAMPLE 1

A–E (Table 1, above) were tested for hyperemia in the guinea pig. The objective of the guinea pig conjunctival hyperemia model is to provide a primary screening indication of the potential of a prostaglandin for inducing conjunctival hyperemia in humans.

Guinea pigs were maintained in their cages during the study, and removed only for scoring and dosing. Eyes were evaluated using a magnifying lens with fluorescent illumi- Scores of 0 or 1 indicated no hyperemia, and scores of 2–4 indicated hyperemia (a score of 4 indicating the most hyperemia). Only integer scores were permitted in order to minimize subjectivity.

Baseline observations were made prior to unilateral dosing with a 10 μl aliquot of either the prostaglandin test formulation or the control formulation, followed by observations at 1, 2, 3 and 4 hours after dosing. Groups typically contained four animals, but ranged up to eight animals per group. The results of the study are presented in Table 2, below, as percent frequency of each score, and in FIG. 1 as percent incidence of hyperemia, defined as the percent of scores of +2 or +3 relative to the total number of observations for each dose.

TABLE 2

Guinea Pig Conjunctival Hyperemia**

| Compound (isopropyl ester) | Prostaglandin Dose | | | | | | | | | | | | | | | | | | | |
|---|---|---|---|---|---|---|---|---|---|---|---|---|---|---|---|---|---|---|---|---|
| | 0.03 µg | | | | | 0.1 µg | | | | | 0.3 µg | | | | | 1.0 µg | | | | |
| | Score | | | | | Score | | | | | Score | | | | | Score | | | | |
| | 0 | 1 | 2 | 3 | N* | 0 | 1 | 2 | 3 | N* | 0 | 1 | 2 | 3 | N* | 0 | 1 | 2 | 3 | N* |
| A (Cloprostenol) | 40 | 60 | 0 | 0 | 5 | 60 | 33 | 7 | 0 | 23 | 23 | 61 | 13 | 3 | 21 | 18 | 59 | 19 | 4 | 23 |
| B (Fluprostenol) | 17 | 70 | 13 | 0 | 6 | 12 | 88 | 0 | 0 | 6 | 17 | 50 | 29 | 4 | 6 | 21 | 60 | 13 | 6 | 12 |
| C (16-Phenoxy-17,18,19,20-tetranor PGF$_{2\alpha}$) | 33 | 54 | 13 | 0 | 6 | 4 | 71 | 25 | 0 | 6 | 0 | 0 | 62 | 38 | 6 | 0 | 4 | 33 | 63 | 6 |
| D (17-Phenyl-18,19-20-trinor PGF$_{2\alpha}$) | 46 | 54 | 0 | 0 | 6 | 23 | 62 | 13 | 2 | 12 | 10 | 61 | 27 | 2 | 12 | 15 | 56 | 17 | 12 | 12 |
| E (13,14-Dihydro-17-phenyl-18,19,20-trinor PGF$_{2\alpha}$) | 80 | 20 | 0 | 0 | 5 | 75 | 25 | 0 | 0 | 5 | 40 | 60 | 0 | 0 | 5 | 39 | 56 | 6 | 0 | 9 |

*Number of animals tested
**Numbers indicate percent incidence for that score

Discussion:

C (16-phenoxy-17, 18, 19,20-tetranor PGF$_{2\alpha}$, isopropyl ester) produces significant hyperemia at low doses, and at 0.3 and 1.0 lag doses, all eyes received one or more scores of +3. D (1 7-phenyl-18, 19,20-trinor PGF$_{2\alpha}$, isopropyl ester) produces less hyperemia than C, but significantly more than E (13, 14-dihydro-17-phenyl-18,19,20-trinor PGF$_{2\alpha}$, isopropyl ester), which produces only mild hyperemia. The hyperemia produced by A (cloprostenol, isopropyl ester) and B (fluprostenol, isopropyl ester) appear to be intermediate between that of D and E, but this degree of hyperemia is also mild, and cannot be distinguished from that produced by E.

EXAMPLE 2

In the study presented below, A–E (Table 1, above) were tested for IOP-lowering effect in cynomolgus monkey eyes.

Figure 2:
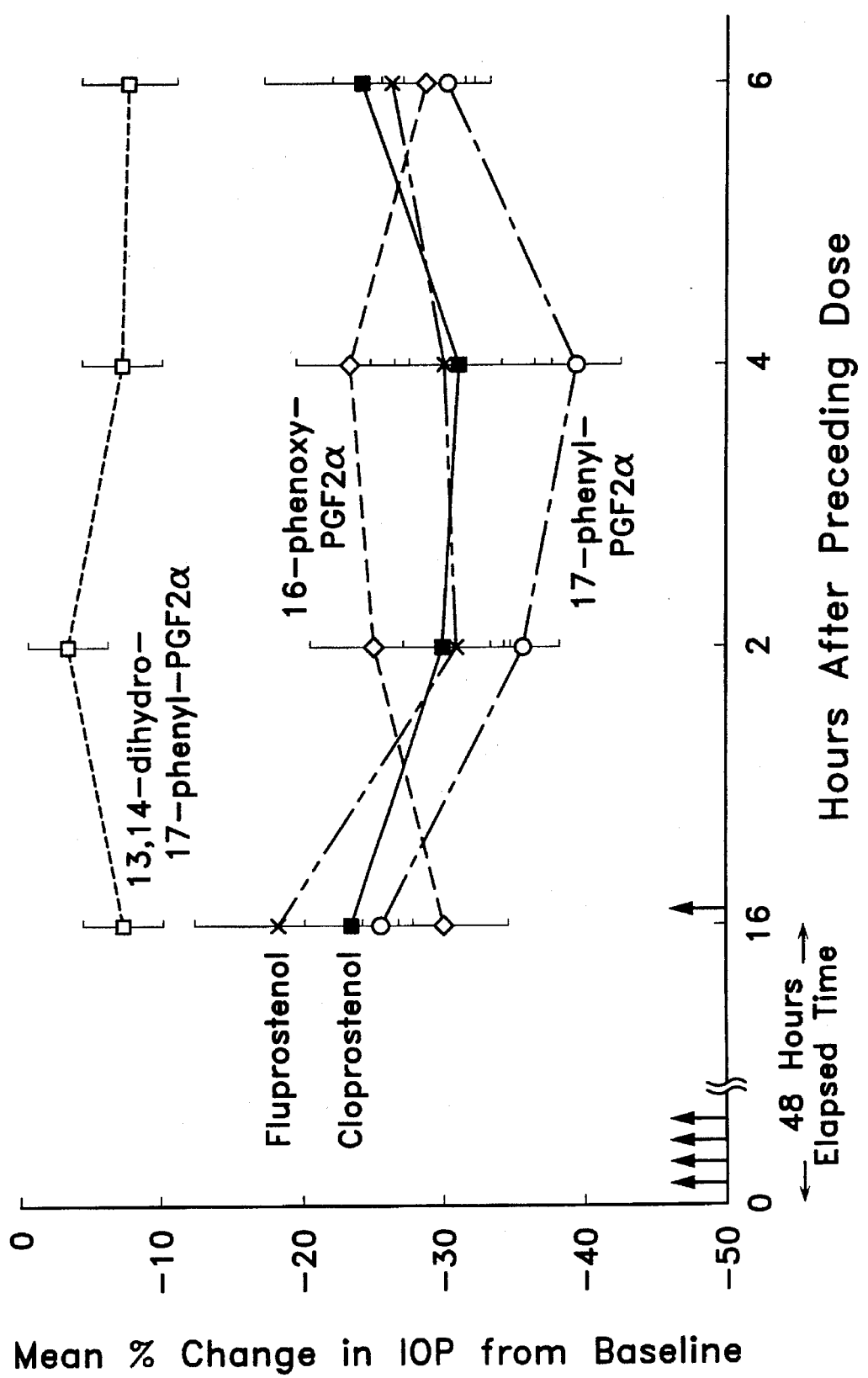
FIG. 2 is a graph showing the relative IOP-lowering effects of five tested compounds (see Table 1, below), two of which are compounds of the present invention. The concentration for each of the tested compounds was 0.3 μg.
Figure 3:
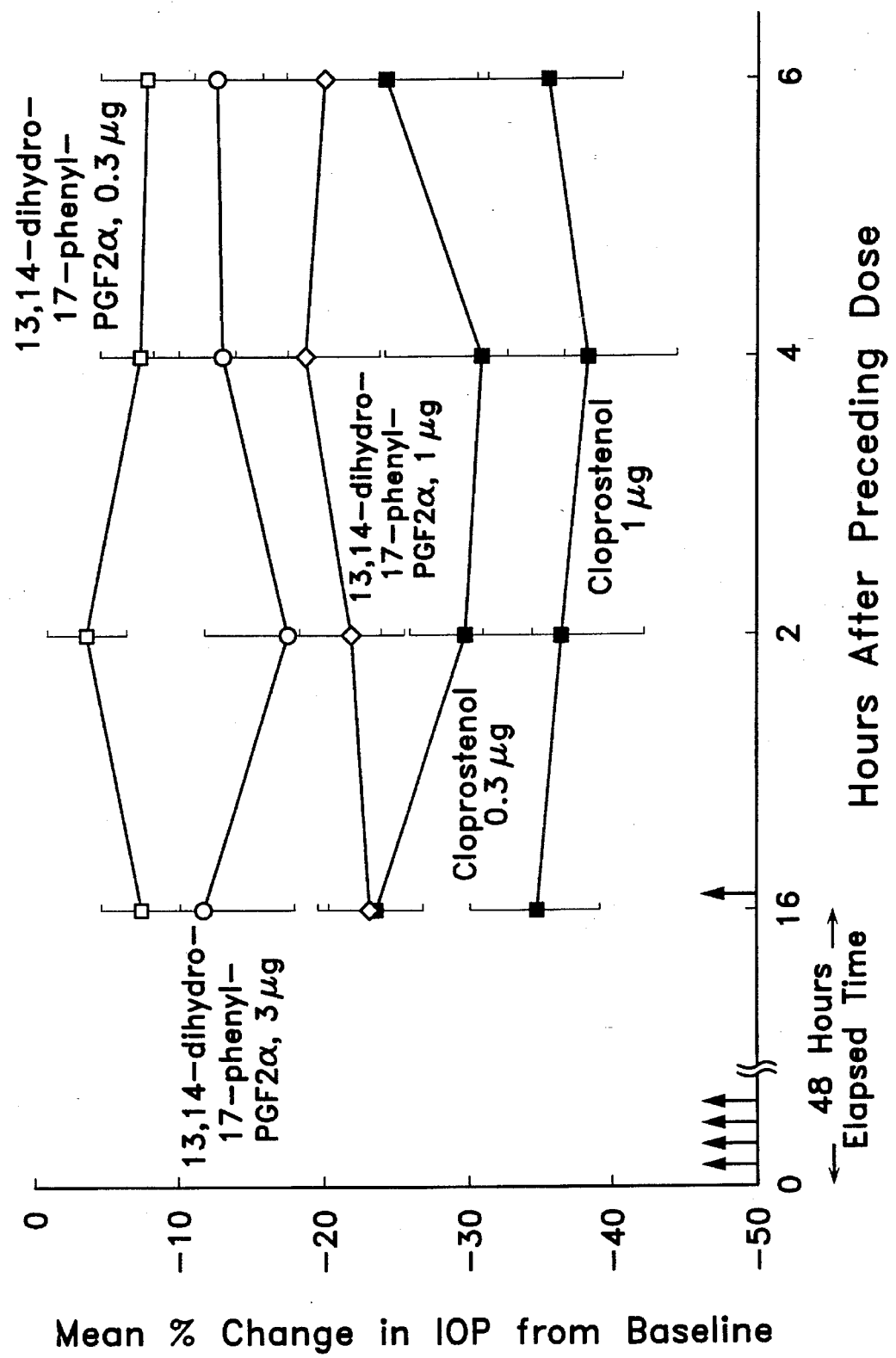
FIG. 3 is a graph similar to that of FIG. 2, showing relative IOP-lowering effects of different concentrations of A (cloprostenol, isopropyl ester) and E (13, 14-dihydro-17-phenyl-18,19,20-trinor $PGF_{2\alpha}$, isopropyl ester).

The right eyes of the cynomolgus monkeys used in this study were previously given laser trabeculoplasty to induce ocular hypertension in the lasered eye. Animals had been trained to sit in restraint chairs and conditioned to accept experimental procedures without chemical restraint. IOP was determined with a pneumatonometer after light corneal anesthesia with dilute proparacaine. The test protocol included a five-dose treatment regimen because of the typical delayed response to prostaglandins. The designated test formulations were administered to the lasered right eyes, and the normal left eyes remained untreated, although IOP measurements were taken. Baseline IOP values were determined prior to treatment with the test formulation, and then IOP was determined from 1 to 7 hours after the first dose, 16 hours after the fourth dose, and 1 to 4 hours after the fifth dose. Results are presented in Tables 3 and 4, below, and in FIGS. 2 and 3, as the mean percent reduction of IOP from baseline + SEM. Prostaglandin doses are micrograms of compound contained in each treatment with 10 µL of the test formulation. In Table 3, the same amount (0.3 Pg) of each of A-E were compared for IOP reduction. In Table 4, various amounts of A (0.3 and 1.0 µg) were compared against various amounts of E (0.3, 1.0 and 3.0 µg) in order to determine the dose responses of the two different compounds.

TABLE 3

Percent IOP Reduction in Lasered Cynomolgus Monkeys

| Compound (isopropyl ester) | Baseline IOP (mm Hg) | Percent IOP Reduction (Hours after Last Dose/Dose #) | | | |
|---|---|---|---|---|---|
| | | 16/4 | 2/5 | 4/5 | 6/5 |
| A (Cloprostenol) | 36.9 | 23.6 ± 3.3 | 30.2 ± 4.5 | 31.2 ± 6.8 | 24.4 ± 6.9 |
| B (Fluprostenol) | 41.6 | 18.4 ± 5.9 | 31.2 ± 3.7 | 30.3 ± 3.8 | 26.6 ± 3.6 |
| C (16-Phenoxy-17,18,19,20-tetranor PGF$_{2\alpha}$) | 38.2 | 30.2 ± 4.4 | 25.3 ± 4.5 | 23.6 ± 3.8 | 28.9 ± 3.0 |
| D (17-Phenyl-18,19,20-trinor PGF$_{2\alpha}$) | 40.8 | 25.6 ± 2.6 | 36.0 ± 2.4 | 39.8 ± 3.1 | 30.3 ± 2.8 |
| E (13,14-Dihydro-17-phenyl-18,19,20-trinor PGF$_{2\alpha}$) | 39.7 | 7.6 ± 2.9 | 3.6 ± 2.7 | 7.5 ± 2.7 | 8.0 ± 3.4 |

TABLE 4

Comparison of Percent IOP Reduction

| Compound | Dose (µg) | Baseline IOP (mm Hg) | Percent IOP Reduction (Hours after Last Dose/Dose #) | | | |
|---|---|---|---|---|---|---|
| | | | 16/4 | 2/5 | 4/5 | 6/5 |
| A* | 0.3 | 36.9 | 23.6 ± 3.3 | 30.2 ± 4.5 | 31.2 ± 6.8 | 24.4 ± 6.9 |
| A | 1 | 39.6 | 34.8 ± 4.5 | 36.7 ± 5.8 | 38.7 ± 5.9 | 35.8 ± 5.1 |
| E | 0.3 | 39.7 | 7.6 ± 2.9 | 3.6 ± 2.7 | 7.5 ± 2.7 | 8.0 ± 3.4 |
| E** | 1 | 38.9 | 23.2 ± 3.6 | 22.0 ± 4.0 | 18.8 ± 5.2 | 20.2 ± 4.0 |
| E | 3 | 30.1 | 11.6 ± 6.5 | 17.6 ± 5.8 | 13.1 ± 5.0 | 12.7 ± 5.0 |

*Cloprostenol, isopropyl ester
**13,14-Dihydro-17-phenyl-18,19,20-trinor PGF$_{2\alpha}$, isopropyl ester

Discussion:

Table 3 shows that A, B, C, and D produce similar degrees of IOP reduction with 0.3 μg doses; however, E is essentially inactive at this dose.

In Table 4, it is apparent that the IOP reduction with 1 μg of A is greater than that produced by 0.3 μg of A, and the response to either of these doses of A is greater than the maximum reduction produced by either dose of E. These observations indicate that A (cloprostenol, isopropyl ester) is both more potent and produces a greater maximum response for IOP reduction than E (13, 14-dihydro-17-phenyl- 18, 19,20-trinor $PGF_{2\alpha}$).

EXAMPLE 3

The following Formulations 1–4 are representative pharmaceutical compositions of the invention for topical use in lowering of intraocular pressure. Each of Formulations 1 through 4 may be formulated in accordance with procedures known to those skilled in the art.

| FORMULATION 1 | |
|---|---|
| Ingredient | Amount (wt %) |
| (I), $R^1 = CH(CH_3)_2$; $R^2 = Cl$ | 0.002 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCl and/or NaOH | pH 7.2–7.5 |
| Purified water | q.s. to 100% |

| FORMULATION 2 | |
|---|---|
| Ingredient | Amount (wt %) |
| (I), $R^1 = C(CH_3)_3$; $R^2 = Cl$ | 0.01 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.01 |
| Benzalkonium chloride | 0.02 |
| Polysorbate 80 | 0.15 |
| HCl and/or NaOH | pH 7.3–7.4 |
| Purified water | q.s. to 100% |

| FORMULATION 3 | |
|---|---|
| Ingredient | Amount (wt %) |
| (I), $R^1 = CH_3$; $R^2 = Cl$ | 0.001 |
| Dextran 70 | 0.1 |
| Hydroxypropyl methylcellulose | 0.5 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Benzalkonium chloride | 0.01 |
| NaOH and/or HCl | pH 7.3–7.4 |
| Purified water | q.s. to 100% |

| FORMULATION 4 | |
|---|---|
| Ingredient | Amount (wt %) |
| (I), $R^1 = CH_2CH_3$; $R^2 = Cl$ | 0.003 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Benzalkonium chloride | 0.01 |
| HCl and/or NaOH | pH 7.3–7.4 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises topically administering to the affected eye a therapeutically effective amount of a compound of formula:

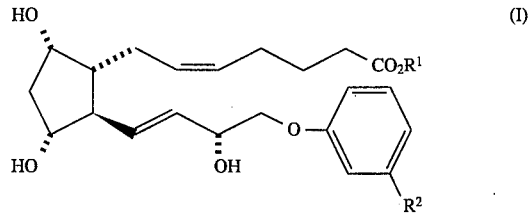

wherein: $R^1$=hydrogen, a cationic salt moiety, a pharmaceutically acceptable amine moiety or $C_1$–$C_{12}$ alkyl, cycloalkyl or aryl; and $R^2$=Cl or $CF_3$.

2. The method of claim 1, wherein $R^1$ is selected from the group consisting of H, $CH_3$, $CH(CH_3)_2$ and $C(CH_3)_3$.

3. The method of claim 1, wherein $R^1$ is selected from the group consisting of $Na^+$ and $CH_3N^+(CH_2OH)_3$.

4. The method of claim 1, wherein $R^2$ is Cl.

5. The method of claim 1, wherein $R^2$ is $CF_3$.

6. The method of claim 1, wherein between about 0.001 and about 1000 μg/eye of a compound of formula (I) is administered.

7. The method of claim 6, wherein between about 0.01 and about 100 μg/eye of a compound of formula (I) is administered.

8. The method of claim 6, wherein between about 0,05 and about 10 μg/eye of a compound of formula (I) is administered.

9. A topical ophthalmic composition for the treatment of glaucoma and ocular hypertension in primates, comprising a therapeutically effective amount of a compound of formula:

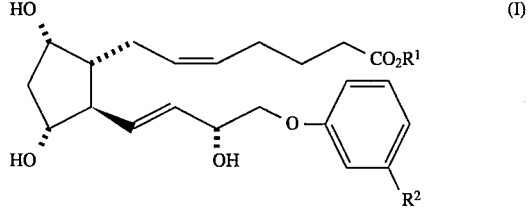

wherein: $R^1$=hydrogen, a cationic salt moiety, a pharmaceutically acceptable amine moiety or $C_1$–$C_{12}$ alkyl, cycloalky or aryl; and $R^2$=Cl or $CF_3$.

10. The composition of claim 9, wherein $R^1$ is selected from the group consisting of H, $CH_3$, $CH(CH_3)_2$ and $C(CH_3)_3$.

11. The composition of claim 9, wherein $R^1$ is selected from the group consisting of $Na^+$ and $CH_3N^+(CH_2OH)_3$.

12. The composition of claim 9, wherein $R^2$ is Cl.

13. The composition of claim 9, wherein $R^2$ is $CF_3$.

14. The composition of claim 9, wherein between about 0.001 and about 100 µg/eye of a compound of formula (I) is administered.

15. The composition of claim 14, wherein between about 0.01 and about 100 µg/eye of a compound of formula (I) is administered.

16. The composition of claim 15, wherein between about 0.05 and about 10 µg/eye of a compound of formula (I) is administered.

17. A method of treating glaucoma and ocular hypertension, which comprises topically administering to the affected eye a therapeutically effective amount of a compound of formula:

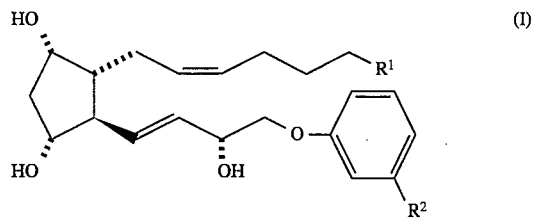

wherein: $R^1$=a pharmaceutically acceptable ester moiety; and $R^2$=Cl or $CF_3$.

18. The method of claim 17, wherein $R^2$ is Cl.

19. The method of claim 17, wherein $R^2$ is $CF_3$.

20. The method of claim 17, wherein between about 0.001 and about 1000 µg\eye of a compound of formula (I) is administered.

* * * * *